(12) United States Patent
Zhang et al.

(10) Patent No.: US 9,824,790 B2
(45) Date of Patent: Nov. 21, 2017

(54) FIRE THROUGH ALUMINUM PASTE FOR $SIN_x$ AND BETTER BSF FORMATION

(75) Inventors: Dongshe Zhang, Carlsbad, CA (US); Aziz S. Shaikh, San Diego, CA (US); Srinivasan Sridharan, Strongsville, OH (US); Himal Khatri, Vista, CA (US); Hong Jiang, Irvine, CA (US); George E. Graddy, Jr., Del Mar, CA (US)

(73) Assignee: Heraeus Precious Metals North America Conshohocken LLC, West Conshohocken, PA (US)

( * ) Notice: Subject to any disclaimer, the term of this patent is extended or adjusted under 35 U.S.C. 154(b) by 47 days.

(21) Appl. No.: 14/240,788

(22) PCT Filed: Aug. 16, 2012

(86) PCT No.: PCT/US2012/051020
§ 371 (c)(1),
(2), (4) Date: Sep. 2, 2014

(87) PCT Pub. No.: WO2013/032716
PCT Pub. Date: Mar. 7, 2013

(65) Prior Publication Data
US 2014/0373909 A1     Dec. 25, 2014

Related U.S. Application Data

(60) Provisional application No. 61/527,640, filed on Aug. 26, 2011.

(51) Int. Cl.
*H01L 31/00*     (2006.01)
*H01B 1/22*      (2006.01)
(Continued)

(52) U.S. Cl.
CPC .................. *H01B 1/22* (2013.01); *C03C 8/08* (2013.01); *C03C 8/10* (2013.01); *C03C 8/16* (2013.01);
(Continued)

(58) Field of Classification Search
CPC combination set(s) only.
See application file for complete search history.

(56) References Cited

U.S. PATENT DOCUMENTS 4,279,785 A       7/1981    Stewart et al.
4,563,500 A  *    1/1986    Haaf et al. ...................... 525/99
(Continued)

FOREIGN PATENT DOCUMENTS

CN      101785113 A    7/2010
EP      2351717 A1     8/2011
(Continued)

OTHER PUBLICATIONS

English Translation of relevant part of Iwanami, Rikagaku Jiten (Dictionary of Physics and Chemistry), 5th Edition, 1998, p. 1479.

*Primary Examiner* — Eli Mekhlin
(74) *Attorney, Agent, or Firm* — Blank Rome LLP; Charles R. Wolfe, Jr.; Francine F. Li (57) ABSTRACT

Paste compositions, methods of making a paste composition, photovoltaic cells, and methods of making a photovoltaic cell contact are disclosed. The paste composition can include a conductive metal component such as aluminum, phosphate glass, phosphorus compounds such as alkyl phosphate, and a vehicle. The contact can be formed on a passivation layer on a silicon wafer by applying the paste on the passivation layer and firing the paste. During firing, the metal component can fire through the passivation layer, thereby electrically contacting the silicon substrate.

17 Claims, 2 Drawing Sheets

(51) Int. Cl.

| | | |
|---|---|---|
| *C07F 9/11* | (2006.01) | |
| *C03C 8/16* | (2006.01) | |
| *C03C 8/18* | (2006.01) | |
| *C03C 8/22* | (2006.01) | |
| *H01L 31/0224* | (2006.01) | |
| *H01L 21/22* | (2006.01) | |
| *C03C 8/10* | (2006.01) | |
| *C03C 8/08* | (2006.01) | |

(52) U.S. Cl.
CPC ............... *C03C 8/18* (2013.01); *C03C 8/22* (2013.01); *C07F 9/11* (2013.01); *H01L 21/2225* (2013.01); *H01L 31/022425* (2013.01); *H01L 31/022441* (2013.01); *Y02E 10/50* (2013.01)

(56) References Cited

U.S. PATENT DOCUMENTS

| | | | |
|---|---|---|---|
| 8,053,867 B2* | 11/2011 | Huang et al. ................ 257/607 | |
| 8,236,598 B2* | 8/2012 | Khadilkar ............... C03C 3/066 | |
| | | | 136/256 |
| 8,309,844 B2 | 11/2012 | Merchant et al. | |
| 8,778,232 B2 | 7/2014 | Suzuki et al. | |
| 2007/0207565 A1 | 9/2007 | Kodas et al. | |
| 2007/0286973 A1 | 12/2007 | Sawai et al. | |
| 2008/0053592 A1 | 3/2008 | Khadilkar et al. | |
| 2008/0099715 A1* | 5/2008 | Adams ................... C08K 3/32 | |
| | | | 252/62.54 |
| 2008/0260979 A1* | 10/2008 | Yokoyama et al. ......... 428/35.7 | |
| 2009/0056798 A1 | 3/2009 | Merchant et al. | |
| 2009/0120490 A1* | 5/2009 | Huang et al. ................. 136/252 | |
| 2009/0142880 A1 | 6/2009 | Weidman et al. | |
| 2009/0173379 A1* | 7/2009 | Kim ............................. 136/256 | |
| 2010/0095705 A1 | 4/2010 | Burkhalter et al. | |
| 2010/0151323 A1 | 6/2010 | Naito et al. | |
| 2010/0173446 A1* | 7/2010 | Khadilkar et al. ............. 438/72 | |
| 2010/0275987 A1* | 11/2010 | Sakamoto ......... H01L 31/03529 | |
| | | | 136/256 |
| 2011/0180137 A1* | 7/2011 | Iwamuro et al. ............. 136/256 | |
| 2012/0012178 A1* | 1/2012 | Chuang ................... H01B 1/16 | |
| | | | 136/256 |
| 2012/0017986 A1* | 1/2012 | Nakatani ......... H01L 31/022425 | |
| | | | 136/256 |
| 2012/0031484 A1* | 2/2012 | Matsuno et al. ............. 136/256 | |

FOREIGN PATENT DOCUMENTS

| | | | | |
|---|---|---|---|---|
| JP | 55-75937 A | 6/1980 | | |
| JP | 04270140 A | 9/1992 | | |
| JP | 2008-254974 A | 10/2008 | | |
| JP | 2009124148 A | 6/2009 | | |
| JP | 2010161331 S | 7/2010 | | |
| JP | WO 2010119512 A1 * | 10/2010 | ..... H01L 31/022425 |
| JP | 2010538466 A | 12/2010 | | |
| JP | 2010538471 A | 12/2010 | | |
| JP | 2011066044 A | 3/2011 | | |
| TW | 200849615 A | 12/2008 | | |
| WO | WO-2009/032429 A1 | 3/2009 | | |
| WO | WO-2011/013440 A1 | 2/2011 | | |
| WO | WO-2011090215 A1 | 7/2011 | | |

* cited by examiner

FIRE THROUGH ALUMINUM PASTE FOR SIN$_x$ AND BETTER BSF FORMATION

TECHNICAL FIELD

The subject disclosure generally relates to paste compositions, methods of making a paste composition, photovoltaic cells, and methods of making a photovoltaic cell contact.

BACKGROUND

Solar cells are generally made of semiconductor materials, such as silicon (Si), which convert sunlight into useful electrical energy. Solar cells are typically made of thin wafers of Si in which the required PN junction is formed by diffusing phosphorus (P) from a suitable phosphorus source into a P-type Si wafer. The side of silicon wafer on which sunlight is incident is in general coated with an anti-reflective coating (ARC) to prevent reflective loss of incoming sunlight, and thus to increase the efficiency of the solar cell. A two dimensional electrode grid pattern known as a front contact makes a connection to the N-side of silicon, and a coating of aluminum (Al) on the other side (back contact) makes connection to the P-side of the silicon. These contacts are the electrical outlets from the PN junction to the outside load.

Front and back contacts of silicon solar cells are typically formed by screen-printing a thick film paste. Typically, the front paste contains approximately fine silver particles, glass and organics. After screen-printing, the wafer and paste are fired in air, typically at furnace set temperatures of about 650-1000° C. During the firing, glass softens, melts, and reacts with the anti-reflective coating, etches the silicon surface, and facilitates the formation of intimate silicon-silver contact. Silver deposits on silicon as islands. The shape, size, and number of silicon-silver islands determine the efficiency of electron transfer from silicon to the outside circuit.

The back side of the silicon wafer typically includes Al paste, but generally lacks an ARC. Conventional back Al pastes do not fire through typical ARC materials such as SiN$_x$, SiO$_2$, and TiO$_2$. Conversely, pastes that fire through well on the front side of silicon do not form a Back Surface Field (BSF) layer, and are hence unsuitable for use in solar cell back contacts.

SUMMARY

The following presents a simplified summary of the invention in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In accordance with one aspect, a paste composition is provided. More particularly, in accordance with this aspect, the paste composition includes a conductive metal component, phosphate glass, at least one phosphorus compound, and a vehicle. The phosphorous compound is selected from the group consisting of ammonium phosphates, organic phosphates, ammonium salts of organic phosphates, alkali metal salts of organic phosphates, alkaline earth metal salts of organic phosphates, ammonium phosphonates, organic phosphonates, ammonium salts of organic phosphonates, alkali metal salts of organic phosphonates, alkaline earth metal salts of organic phosphonates, ammonium hypophosphites, organic hypophosphites, ammonium salts of organic hypophosphites, alkali metal salts of organic hypophosphites, and alkaline earth meal salts of organic hypophosphites.

In accordance with another aspect, a photovoltaic cell is provided. More particularly, in accordance with this aspect, the photovoltaic cell includes a silicon wafer and a back contact thereon, the back contact including a passivation layer at least partially coated with a back side paste. The back side paste includes, prior to firing, a conductive metal component, phosphate glass, at least one phosphorus compound, and vehicle. The phosphorous compound is selected from the group consisting of ammonium phosphates, organic phosphates, ammonium salts of organic phosphates, alkali metal salts of organic phosphates, alkali earth metal salts of organic phosphates, ammonium phosphonates, organic phosphonates, ammonium salts of organic phosphonates, alkali metal salts of organic phosphonates, alkaline earth metal salts of organic phosphonates, ammonium hypophosphites, organic hypophosphites, ammonium salts of organic hypophosphites, alkali metal salts of organic hypophosphites, and alkali earth meal salts of organic hypophosphites.

In accordance with yet another aspect, a method of making a paste composition is provided. More particularly, in accordance with this aspect, the method involves combining a conductive metal component, phosphate glass, a phosphorus compound, and a vehicle, and dispersing the conductive metal component, the phosphate glass, and the phosphorus compound in the vehicle.

In accordance with still yet another aspect, a method of forming a photovoltaic cell contact is provided. More particularly, in accordance with this aspect, the method involves providing a silicon substrate and a passivation layer thereon; applying a paste composition on the passivation layer, the paste including a conductive metal component phosphate glass, a phosphorus compound, and a vehicle; and heating the paste to sinter the conductive metal component and fuse the glass. The conductive metal component can fire through the passivation layer, thereby electrically contacting the silicon substrate.

To the accomplishment of the foregoing and related ends, the invention, then, involves the features hereinafter fully described and particularly pointed out in the claims. The following description and the annexed drawings set forth in detail certain illustrative embodiments of the invention. These embodiments are indicative, however, of but a few of the various ways in which the principles of the invention can be employed. Other objects, advantages and novel features of the invention will become apparent from the following detailed description of the invention when considered in conjunction with the drawings.

BRIEF DESCRIPTION OF THE DRAWINGS

FIGS. 1-5 provide a process flow diagram schematically illustrating the fabrication of a semiconductor device. Reference numerals shown in FIGS. 1-5 are explained below.
100: p-type silicon substrate
200: n-type diffusion layer
300: front side passivation layer/anti-reflective coating (e.g., SiN$_x$, TiO$_2$, SiO$_2$ film)
302: back side passivation layer (e.g., SiN$_x$ TiO$_2$, SiO$_2$ film)
400: aluminum back paste formed on backside

402: silver or silver/aluminum back paste formed on backside
404: gap between back pastes
406: silver paste formed on front side
500: aluminum back electrode after firing showing fire through of passivation layer and BSF formation
502: p+ layer (back surface field, BSF)
504: silver or silver/aluminum back electrode (obtained by firing silver or silver/aluminum back paste)
506: silver front electrode after firing through ARC

DETAILED DESCRIPTION

Back contacts on $Si_3N_4$ back passivated cells are conventionally made by first etching a hole through a passivation layer either by laser or by chemical etching using acids such as HF and hot $H_3PO_4$, and then screen printing and firing an aluminum back contact paste. This involves two steps, i.e., etching the hole through the passivation layer and screen printing and firing the Al back paste. The etching hole process is time-consuming and costly. One objective of the subject invention is to reduce this to one step using a paste that can fire through as well as react with silicon and create a BSF layer in the back side of wafer silicon.

The subject invention can overcome the shortcomings of the conventional methods of making the back contacts. The subject invention generally relates to paste compositions, photovoltaic cells including fired paste compositions, methods of making a paste composition, methods of making a photovoltaic cell including a fired paste composition. The paste compositions can be used to form a contact, which can be used in solar cells as well as other related components. The subject invention can provide one or more of the following advantages: 1) there is no need to make a hole through a passivation layer; 2) the BSF formation and/or Al—Si eutectic formation is uniform and fully developed; and therefore 3) there are no wide variations in the efficiency of cells achieved.

The paste composition can include a conductive metal component, phosphate glass, at least one phosphorus compound, and a vehicle. The phosphorous compound can be selected from the group consisting of ammonium phosphates, organic phosphates, ammonium salts of organic phosphates, alkali metal salts of organic phosphates, alkaline earth metal salts of organic phosphates, ammonium phosphonates, organic phosphonates, ammonium salts of organic phosphonates, alkali metal salts of organic phosphonates, alkaline earth metal salts of organic phosphonates, ammonium hypophosphites, organic hypophosphites, ammonium salts of organic hypophosphites, alkali metal salts of organic hypophosphites, and alkaline earth meal salts of organic hypophosphites.

The paste composition can achieve fire-through of the backside ARC forming the BSF in silicon solar cells. The ARC can include any or all of SiNx, Al2O3, SiO2, TiO2, Al2O3/SiNx, SiO2/SiNx etc. and also serves as the passivation layer. The terms "ARC" and "passivation layer" will be used interchangeably herein.

The paste formulations are generally screen printable and suitable for use in photovoltaic devices. However, other application procedures can be used such as spraying, hot melt printing, pad printing, ink-jet printing, and tape lamination techniques with suitable modifications of the vehicle component. In one embodiment, two paste compositions are applied onto a substrate by sequential double printing. The paste composition can form a conductive thick film on a substrate. The conductive thick film can permit good fire-through of the backside passivation layer by the Al paste and effective formation of a BSF layer at the silicon-aluminum interface. Broadly, the subject thick film pastes can be used to make back contacts for silicon-based solar cells to conduct to an external load the current generated by exposure to light.

The pastes herein can be used to form conductors in applications other than solar cells, and employing other substrates, such as, for example, glass, ceramics, enamels, alumina, and metal core substrates. For example, the paste is used in devices including MCS heaters, LED lighting, thick film hybrids, fuel cell systems, automotive electronics, and automotive windshield busbars.

The pastes can be prepared either by mixing individual components (i.e., metals, glass frits, phosphorous compounds, and vehicles) or by blending pastes that are Al based (major component) with phosphorous compounds that achieve the desired objectives. Broadly construed, the inventive pastes include a conductive metal including at least aluminum, glass, a phosphorous compound, and a vehicle. Each ingredient is detailed hereinbelow.

Metal Component

The conductive metal component can include aluminum. In one embodiment, the major metal component of the fire-through paste is aluminum. Aluminum is used because it forms a low contact resistance p+/p surface on n-type silicon and provides a BSF for enhancing solar cell performance. In one embodiment, the backside fire-through pastes of the invention include about 40 to about 80 wt % aluminum, preferably about 60 to about 80 wt % aluminum and more preferably about 65 to about 75 wt % aluminum.

The paste can include other metals and/or alloys to penetrate the non-conducting passivation layer. The other metals and alloys can include any suitable conductive metal(s) other than aluminum. In one embodiment, the other metals and alloys can be at least one other metal selected from the group consisting of sixteen metals: palladium, silver, platinum, gold, boron, gallium, indium, zinc, tin, antimony, magnesium, potassium, titanium, vanadium, nickel, and copper.

The conductive metal component can include the other metals or alloys at any suitable amount so long as the other metals or alloys can aid in achieving aluminum fire-through of the passivation layer. In one embodiment, the conductive metal component includes about 0.1 to about 50 wt % the other metals or alloys. In another embodiment, the metal component includes about 0.5 to about 50 wt %, 1 to about 25 wt %, more preferably about 2 to about 10 wt % of silver. In yet another embodiment, the metal component includes about 3 to about 50 wt %, preferably about 3 to about 15 wt %, more preferably about 3 to about 10 wt % copper. In still yet another embodiment, the metal component includes about 1 to about 50 wt %, preferably about 5 to about 25 wt %, and more preferably about 5 to about 15 wt % nickel. In another embodiment, the metal component includes about 1 to about 50 wt %, preferably about 3 to about 25 wt %, more preferably about 5 to about 15 wt % magnesium. In yet another embodiment, the metal component includes about 1 to about 50 wt %, preferably about 5 to about 25 wt % boron. In still yet another embodiment, the metal component includes about 1 to about 50 wt %, preferably about 5 to about 25 wt %, and more preferably about 5 to about 15 wt % vanadium. Contacts and solar cells including the above metals are envisioned herein.

All metals herein can be provided in one or more of several physical and chemical forms. Broadly, metal powders, flakes, salts, oxides, glasses, colloids, and organometallics are suitable. The conductive metal component can have any suitable form. The particles of the conductive metal component can be spherical, flaked, colloidal, amorphous, or combinations thereof. In one embodiment, the conductive metal component can be coated with various materials such as phosphorus. Alternately, the conductive metal component can be coated on glass. Aluminum oxide and/or silver oxide can be dissolved in glass during a glass melting/manufacturing process.

The conductive metal component can have any suitable size particle. Generally, the sizes of the conductive metal component particles are about 0.1 to about 40 microns, preferably about 0.1 to about 10 microns. In one embodiment, the Al particles are generally about 2 to about 20 microns, preferably, about 3 to about 10 microns. In another embodiment, the other metal particles are about 2 to about 20 microns, more preferably about 2 to about 8 microns. In yet another embodiment, the metal particle sizes are in line with the sizes of aluminum and silver particles herein, in a back contact. In still yet another embodiment, Al and other metals/alloys have 99+% purity to optimize solar cell electrical performance.

In one embodiment, the metal components can be provided in the form of ionic salts, such as halides, carbonates, hydroxides, phosphates, nitrates, sulfates, and sulfites, of the metal of interest. Organometallic compounds of any of the metals can be used, including acetates, formates, carboxylates, phthalates, isophthalates, terephthalates, fumarates, salicylates, tartrates, gluconates, or chelates such as those with ethylenediamine or ethylenediamine tetraacetic acid (EDTA). Other appropriate powders, salts, oxides, glasses, colloids, and organometallics containing at least one of the sixteen metals will be readily apparent to those skilled in the art. Generally, aluminum and the sixteen metals are provided as metal powders or flakes.

In one embodiment, the metal component include about 80 to about 99 wt % spherical metal particles or alternatively about 35 to about 70 wt % metal particles and about 29 to about 55 wt % metal flakes. In another embodiment, the metal component includes about 75 to about 90 wt % metal flakes and about 5 to about 9 wt % of colloidal metal, or about 60 to about 95 wt % of metal powder or flakes and about 4 to about 20 wt % of colloidal metal. The foregoing combinations of particles, flakes, and colloidal forms of the foregoing metals are not intended to be limiting, where one skilled in the art would know that other combinations are possible. Suitable commercial examples of aluminum particles are available from Alcoa, Inc., Pittsburgh, Pa.; Ampal Inc., Flemington, N.J.; and ECKA Granulate GmbH & Co. KG, of Firth, Germany.

In one embodiment, the metal component includes other conductive metals from groups such as (a) palladium, silver, platinum, gold, and combinations thereof (highly conductive or electrical conduction modifier); (b) boron, gallium, indium, and combinations thereof (trivalent dopants for P type silicon); (c) zinc, tin, antimony, and combinations thereof (low melting metals); and (d) magnesium, titanium, potassium, vanadium, nickel, copper, and combinations thereof (grain modifiers/refiners). Further alloys such as Al—Cu, Al—Mg, Al—Si, Al—Zn, and Al—Ag, and Ag—Pd, Pt—Au, Ag—Pt, can be used for silicon doping. Mixtures of the sixteen metals can also be used for the pastes, contacts, and solar cells herein.

Paste Glasses

The glass can contain one or more suitable glass frits. In one embodiment, the glass used herein is phosphate glass. As an initial matter, the glass frits used in the pastes herein can intentionally contain lead and/or cadmium, or they can be devoid of intentionally added lead and/or cadmium. In one embodiment, the glass frit is a substantially to completely lead-free and cadmium-free glass frit. The glasses can be partially crystallizing or non-crystallizing. In one embodiment partially crystallizing glasses are preferred. The details of the composition and manufacture of the glass frits can be found in, for example, commonly-assigned U.S. Patent Application Publication Nos. 2006/0289055 and 2007/0215202, which are hereby incorporated by reference.

The glass includes, prior to firing, one or more glass frits. In one embodiment, the glass includes $P_2O_5$ or a phosphate glass frit. The glass can include $P_2O_5$: broadly about 1 mole % to about 90 mole %, preferably about 5 mole % to about 80 mole %, preferably about 5 mole % to about 40 mole % and more preferably about 5 mole % to about 25 mole %. In another embodiment, the glass includes PbO, $V_2O_5$, and $P_2O_5$. For example, the glass composition includes PbO: broadly about 1 mole % to about 90 mole %, preferably about 5 mole % to about 80 mole %, alternatively about 10 mole % to about 70 mole %, preferably about 20 mole % to about 50 mole % and more preferably about 20 mole % to about 40 mole %; $V_2O_5$: broadly about 1 mole % to about 90 mole %, preferably about 5 mole % to about 80 mole %, alternatively about 10 mole % to about 70 mole %, preferably about 25 mole % to about 65 mole % and more preferably about 45 mole % to about 65 mole %, and $P_2O_5$: broadly 1 mole % to about 90 mole %, preferably about 5 mole % to about 80 mole %, preferably about 5 mole % to about 40 mole % and more preferably about 5 mole % to about 25 mole %. Specific examples of phosphate glass composition include EG9111 glass powder which is available from Ferro Corporation at Cleveland, Ohio. The EG9111 glass powder includes about 20 to about 25 mole % of PbO, about 55 to about 65 mole % of $V_2O_5$, and about 15 to about 20 mole % of $P_2O_5$.

Combinations of ranges of oxides indicated hereinabove as "broad," "preferably," and "more preferably" in various combinations are available, so long as such combinations of ranges can add up to 100 mole %. For example, the glass includes, prior to firing, about 10 mole % to about 70 mole % of PbO, about 10 mole % to about 70 mole % of $V_2O_5$, and about 5 mole % to about 80 mole % of $P_2O_5$. In another embodiment, the glass includes about 10 mole % to about 70 mole % of PbO, about 25 mole % to about 65 mole % of $V_2O_5$, and about 5 mole % to about 25 mole % $P_2O_5$. In yet another embodiment, the glass includes about 25 mole % to about 50 mole % of PbO, about 45 mole % to about 65 mole % of $V_2O_5$, and about 5 mole % to about 80 mole % $P_2O_5$. In still yet another embodiment, the glass includes about 20 mole % to about 40 mole % of PbO, about 10 mole % to about 70 mole % of $V_2O_5$, and about 5 mole % to about 40 mole % $P_2O_5$.

Table 1 below shows glass frit compositions useful in the practice of the subject invention. The oxide constituent amounts for an embodiment need not be limited to those in a single column such as 1-1, 1-2, 1-3, or 1-4. Oxide ranges from different columns in the same table can be combined so long as the sum of those ranges can add up to 100 mole %.

TABLE 1

Glass Frit Compositions (mole %)

| Ingredient | Glass 1-1 | 1-2 | 1-3 | 1-4 |
|---|---|---|---|---|
| PbO | 1-90 | 10-70 | 20-50 | 20-40 |
| $V_2O_5$ | 1-90 | 10-70 | 25-65 | 45-65 |
| $P_2O_5$ | 5-80 | 5-80 | 5-40 | 5-25 |

The glass frits can be formed by any suitable techniques. In one embodiment, the glass frits are formed by blending the starting materials (e.g., aforementioned oxides) and melting together at a temperature of about 850 to about 1250° C. for about 40 to 60 minutes to form a molten glass having the desired composition. Depending on the raw materials used, amount of glass being melted, and the type of furnace used these ranges will vary. The molten glass formed can then be suddenly cooled by any suitable technique including water quenching to form a frit. The frit can then be ground using, for example, milling techniques to a fine particle size, from about 0.5 to 25 microns, preferably 1 to about 10 microns, alternatively 2 to about 8 microns, and more preferably about 2 to about 6 microns. In one embodiment, the sizes of glass component are about 2 microns to about 20 microns.

The paste composition can contain any suitable amount of the glass binder. In one embodiment, the paste composition contains the glass component at about 0.5 wt % or more and about 10 wt % or less. In another embodiment, the paste composition contains the glass component at about 0.5 wt % or more and about 8 wt % or less. In yet another embodiment, the paste composition contains the glass component at about 0.5 wt % or more and about 5 wt % or less. In still yet another embodiment, the paste composition contains the glass component at about 0.5 wt % or more and about 3 wt % or less.

The glass component can be a single frit or mixture of one or more glass frits. In a preferred embodiment of mixture of glasses at least one glass frit composition will be from Table 1.

In one embodiment, the glass component contains only one transition metal oxide, wherein the metal of the transition metal oxide is selected from the group consisting of Mn, Fe, Co, Ni, Cu, Ti, V, Cr, W, Nb, Ta, Hf, Rh, Ru, Pd, and Pt. In another embodiment, the glass component contains only two transition metal oxides, wherein the metals of the two transition metal oxides are selected from the group consisting of Mn, Fe, Co, Ni, Cu, Ti, V, Cr, W, Nb, Ta, Hf, Rh, Ru, Pd, and Pt. In another embodiment, the glass component contains three or more oxides of transition metal selected from the group consisting of Mn, Fe, Co, Ni, Cu, Ti, V, Cr, W, Nb, Ta, Hf, Rh, Ru, Pd, and Pt. In one embodiment, the glass component contains only transition metal oxides having metal selected from the group consisting of Mn, Fe, Co, Ni, Cu, Ti, V, Cr, W, Nb, Ta, Hf, Rh, Ru, Pd, and Pt, as transition metal oxides, and does not contain any other transition metal oxides. In another embodiment, the glass component contains, as transition metal oxides, only ZnO and the oxides of transition metal selected from the group consisting of Mn, Fe, Co, Ni, Cu, Ti, V, Cr, W, Nb, Ta, Hf, Rh, Ru, Pd, and Pt.

In one embodiment, the glass component includes, prior to firing, Bi—Zn—B glasses. Table 2 below shows some exemplary Bi—Zn—B glasses. The oxide constituent amounts for an embodiment need not be limited to those in a single column such as 2-1 to 2-5.

TABLE 2

Bi—Zn—B glasses in mole percent of glass component.

| Oxide (mole %) | 2-1 | 2-2 | 2-3 | 2-4 | 2-5 |
|---|---|---|---|---|---|
| $Bi_2O_3$ | 25-65 | 30-60 | 32-55 | 35-50 | 37-45 |
| ZnO | 3-60 | 10-50 | 15-45 | 20-40 | 30-40 |
| $B_2O_3$ | 4-65 | 7-60 | 10-50 | 15-40 | 18-35 |

In another embodiment, the glass component includes, prior to firing, Bi—B—Si glasses. Table 3 below shows some exemplary Bi—B—Si glasses. The oxide constituent amounts for an embodiment need not be limited to those in a single column such as 3-1 to 3-5.

TABLE 3

Bi—B—Si glasses in mole percent of glass component.

| Oxide (mole %) | 3-1 | 3-2 | 3-3 | 3-4 | 3-5 |
|---|---|---|---|---|---|
| $Bi_2O_3$ | 25-65 | 30-60 | 32-55 | 35-50 | 37-45 |
| $B_2O_3$ | 4-65 | 7-60 | 10-50 | 15-40 | 18-35 |
| $SiO_2$ | 5-35 | 5-30 | 5-25 | 5-20 | 5-15 |

In yet another embodiment, the glass component includes, prior to firing, Zn—B—Si glasses. Table 4 below shows some exemplary Zn—B—Si glasses. The oxide constituent amounts for an embodiment need not be limited to those in a single column such as 4-1 to 4-5.

TABLE 4

Zn—B—Si glasses in mole percent of glass component.

| Oxide (mole %) | 4-1 | 4-2 | 4-3 | 4-4 | 4-5 |
|---|---|---|---|---|---|
| ZnO | 3-60 | 10-50 | 15-45 | 20-40 | 30-40 |
| $B_2O_3$ | 4-65 | 7-60 | 10-50 | 15-40 | 18-35 |
| $SiO_2$ | 5-35 | 5-30 | 5-25 | 5-20 | 5-15 |

In still yet another embodiment, the glass component includes, prior to firing, alkali-B—Si glasses. Table 5 below shows some exemplary alkali-B—Si glasses. The oxide constituent amounts for an embodiment need not be limited to those in a single column such as 5-1 to 5-5.

TABLE 5

Alkali-B—Si glasses in mole percent of glass component.

| Ingredient (mole %) | 5-1 | 5-2 | 5-3 | 5-4 | 5-5 |
|---|---|---|---|---|---|
| $Li_2O + Na_2O + K_2O$ | 5-55 | 15-50 | 30-40 | 15-50 | 30-40 |
| $TiO_2$ | 0.5-25 | 0.5-20 | 0.5-15 | 1-10 | 1-5 |
| $B_2O_3 + SiO_2$ | 5-75 | 25-70 | 30-52 | 25-70 | 30-52 |
| $V_2O_5 + Sb_2O_5 + P_2O_5$ | 0-30 | 0.25-25 | 5-25 | 0.25-25 | 5-25 |
| $MgO + CaO + BaO + SrO$ | 0-20 | 0-15 | 0-10 | 0-15 | 0-10 |
| F | 0-20 | 0-15 | 5-13 | 0-15 | 5-13 |

In another embodiment, the glass component includes, prior to firing, Bi—Si—V/Zn glasses. Table 6 below shows some exemplary Bi—Si—V/Zn glasses. The oxide constituent amounts for an embodiment need not be limited to those in a single column such as 6-1 to 6-5.

TABLE 6

Bi—Si—V/Zn glasses in mole percent of glass component.

| Oxide (mole %) | 6-1 | 6-2 | 6-3 | 6-4 | 6-5 |
|---|---|---|---|---|---|
| $Bi_2O_3$ | 5-85 | 15-80 | 20-80 | 30-80 | 40-80 |
| $SiO_2$ | 5-35 | 5-30 | 5-25 | 5-20 | 5-15 |
| ZnO | 0-55 | 0.1-40 | 0.1-25 | 1-20 | 1-15 |
| $V_2O_5$ | 0-55 | 0.1-40 | 0.1-25 | 1-20 | 1-15 |

In yet another embodiment, the glass component includes, prior to firing, Pb—Al—B—Si glasses. Table 8 below shows some exemplary Pb—Al—B—Si glasses. The oxide constituent amounts for an embodiment need not be limited to those in a single column such as 7-1 to 7-5.

TABLE 7

Pb—Al—B—Si glasses in mole percent of glass component.

| Oxide (mole %) | 7-1 | 7-2 | 7-3 | 7-4 | 7-5 |
|---|---|---|---|---|---|
| PbO | 30-70 | 35-70 | 40-70 | 50-70 | 60-70 |
| $B_2O_3 + SiO_2$ | 5-35 | 5-30 | 5-25 | 5-20 | 5-15 |
| $Al_2O_3$ | 1-25 | 2-23 | 3-21 | 4-19 | 5-18 |

Although generally avoided due to cost or health reasons, substantial additions of $Tl_2O$ or $TeO_2$ or $GeO_2$ can be present in these glass compositions to attain lower flow temperatures.

Phosphorous Compound

The pastes of the subject invention include one or more phosphorus compounds. The phosphorous compounds can aid in achieving fire-through of the backside passivation layer in silicon solar cells. It is believed that the phosphorous compound can react preferentially with silicon compounds (e.g., $Si_3N_4$ and Si) than aluminum, thereby achieving fire-through of the backside passivation layer.

Examples of phosphorus compounds include ammonium phosphates, organic phosphates, ammonium phosphonates, organic phosphonates, ammonium hypophosphites, and organic hypophosphites. The phosphorous compounds can be selected from the group consisting of ammonium phosphates, organic phosphates, ammonium salts of organic phosphates, alkali metal salts of organic phosphates, alkaline earth metal salts of organic phosphates, ammonium phosphonates, organic phosphonates, ammonium salts of organic phosphonates, alkali metal salts of organic phosphonates, alkaline earth metal salts of organic phosphonates, ammonium hypophosphites, organic hypophosphites, ammonium salts of organic hypophosphites, alkali metal salts of organic hypophosphites, and alkaline earth meal salts of organic hypophosphites. The ammonium hypophosphite can be selected from the group consisting of ammonium dihydrogen phosphate and diammonium hydrogen phosphate. In one embodiment, the paste does not include $H_3PO_4$, $H_3PO_3$, $H_3PO_2$, $H_3PO_9$, $HPO_3$, $H_4P_2O_7$, $H_5P_3O_{10}$, $H_6P_4O_{13}$, or polyphosphoric acid.

The organic phosphates can have the formula $Y_n(XO)_{3-n}P=O$, wherein n=0, 1, or 2, and X and Y are each independently selected from the group consisting of a hydrogen, alkyl, cycloalkyl, aryl, alkaryl, aralkyl, and aromatic group. In one embodiment, when n=0, the organic phosphates have the formula $(XO)_3P=O$, wherein at least one of three Xs is selected from the group consisting of a hydrogen, alkyl, cycloalkyl, aryl, alkaryl, aralkyl, and aromatic group. Examples of organic phosphates include $C_1$ to $C_{20}$ alkyl phosphates, $C_3$ to $C_8$ cycloalkyl phosphates, $C_6$ to $C_{12}$ aryl phosphates, and $C_7$ to $C_{20}$ aralkyl phosphates. Specific examples of organic phosphate include methyl phosphate, dimethyl phosphate, ethyl phosphate, diethyl phosphate, butyl phosphate, dibutyl phosphate, phenyl phosphate, diphenyl phosphate, dibenzyl phosphate, trimethyl phosphate, triphenyl phosphate, diphenyl cresyl phosphate, and methyl diphenyl phosphate.

In another embodiment, when n=1, the organic phosphonates have the formula $Y(XO)_2P=O$, wherein X and Y are each independently selected from the group consisting of a hydrogen, alkyl, cycloalkyl, aryl, alkaryl, aralkyl, and aromatic group. Examples of organic phosphonates include $C_1$ to $C_{20}$ alkyl phosphonates, $C_3$ to $C_8$ cycloalkyl phosphonates, $C_6$ to $C_{12}$ aryl phosphonates, and $C_7$ to $C_{20}$ aralkyl phosphonates. Specific examples of organic phosphonates include methyl phosphonate, dimethyl phosphonate, ethyl phosphonate, diethyl phosphonate, butyl phosphonate, dibutyl phosphonate, phenyl phosphonate, diphenyl phosphonate, dibenzyl phosphonate, and methyl phenyl phosphonate.

In yet another embodiment, when n=2, the organic hypophosphites have the formula $Y_2(XO)P=O$, wherein X and Y are each independently selected from the group consisting of a hydrogen, alkyl, cycloalkyl, aryl, alkaryl, aralkyl, and aromatic group. Examples of organic hypophosphites include $C_1$ to $C_{20}$ alkyl hypophosphites, $C_3$ to $C_8$ cycloalkyl hypophosphites, $C_6$ to $C_{12}$ aryl hypophosphites, and $C_7$ to $C_{20}$ aralkyl hypophosphites. Specific examples of organic hypophosphites include methyl hypophosphite, ethyl hypophosphite, butyl hypophosphite, and phenyl hypophosphite.

Alkali metals of the alkali metal salts of organic phosphates, organic phosphonates, organic hypophosphites are a series of elements selected from Group IA of the Periodic Table of the Elements. Examples of alkali metals include lithium (Li), sodium (Na), potassium (K), rubidium (Rb), cesium (Cs), and francium (Fr). In one embodiment, the alkali metals of alkali metal salts of organic phosphates, organic phosphonates, and organic hypophosphites include Li, Na, K, Rb, Cs, Fr, or combinations thereof.

Alkaline earth metals of the alkaline earth metal salts of organic phosphates, organic phosphonates, and organic hypophosphites are a series of elements selected from Group IIA of the Periodic Table of the Elements. Examples of alkaline earth metals include beryllium (Be), magnesium (Mg), calcium (Ca), strontium (Sr), barium (Ba) and radium (Ra). In one embodiment, the alkaline earth metals of the alkaline earth metal salts of organic phosphates, organic phosphonate, and organic hypophosphites include Be, Mg, Ca, Sr, Ba, Ra, or combinations thereof.

The pastes can include any suitable amount of the phosphorous compounds so long as the pastes can achieve one or more of the advantages as described above. In one embodiment, the pastes include about 0.1 to about 30 wt % of the phosphorus compounds. In another embodiment, the pastes include about 1 to about 25 wt % of the phosphorus compounds. In yet another embodiment, the pastes include about 1 to about 20 wt % of the phosphorus compounds. In still yet another embodiment, the pastes include about 1 to about 15 wt % of the phosphorus compounds. In one embodiment, the pastes include about 1 to about 10 wt % of the phosphorus compounds. The phosphorous compounds can be dissolved and/or dispersed in the vehicle of the paste.

Vehicle

The pastes herein include a vehicle or carrier which is typically a solution of a resin dissolved in a solvent and, frequently, a solvent solution containing both resin and a thixotropic agent. The glass frits can be combined with the vehicle to form a printable paste composition. The vehicle can be selected on the basis of its end use application. In one embodiment, the vehicle adequately suspends the particulates and burn off completely upon firing of the paste on the substrate. Vehicles are typically organic. Examples of organic vehicles include alkyl ester alcohols, terpineols, and dialkyl glycol ethers, pine oils, vegetable oils, mineral oils, low molecular weight petroleum fractions, and the like. In another embodiment, surfactants and/or other film forming modifiers can also be included.

The amount and type of organic vehicles utilized are determined mainly by the final desired formulation viscosity, fineness of grind of the paste, and the desired wet print thickness. In one embodiment, the paste includes about 15 to about 40 wt % of the vehicle. In another embodiment, the paste includes about 20 to about 35 wt % of the vehicle.

The vehicle typically includes (a) at least about 80 wt % organic solvent; (b) up to about 15 wt % of a thermoplastic resin; (c) up to about 4 wt % of a thixotropic agent; and (d) up to about 2 wt % of a wetting agent. The use of more than one solvent, resin, thixotrope, and/or wetting agent is also envisioned. Ethyl cellulose is a commonly used resin. However, resins such as ethyl hydroxyethyl cellulose, wood rosin, mixtures of ethyl cellulose and phenolic resins, polymethacrylates of lower alcohols and the monobutyl ether of ethylene glycol monoacetate can also be used. Solvents having boiling points (1 atm) from about 130° C. to about 350° C. are suitable. Widely used solvents include terpenes such as alpha- or beta-terpineol or higher boiling alcohols such as DOWANOL™ (diethylene glycol monoethyl ether), or mixtures thereof with other solvents such as butyl CARBITOL™ (diethylene glycol monobutyl ether); dibutyl CARBITOL™ (diethylene glycol dibutyl ether), butyl CARBITOL™ acetate (diethylene glycol monobutyl ether acetate), hexylene glycol, TEXANOL™ (2,2,4-trimethyl-1,3-pentanediol monoisobutyrate), as well as other alcohol esters, kerosene, and dibutyl phthalate.

The vehicle can contain organometallic compounds, for example those based on aluminum, boron, zinc, vanadium, or cobalt, and combinations thereof, to modify the contact. N-DIFFUSOL® is a stabilized liquid preparation containing an n-type diffusant with a diffusion coefficient similar to that of elemental phosphorus. Various combinations of these and other solvents can be formulated to obtain the desired viscosity and volatility requirements for each application. Other dispersants, surfactants and rheology modifiers, which are commonly used in thick film paste formulations, can be included. Commercial examples of such products include those sold under any of the following trademarks: TEXANOL™ (Eastman Chemical Company, Kingsport, Tenn.); DOWANOL™ and CARBITOL™ (Dow Chemical Co., Midland, Mich.); TRITON® (Union Carbide Division of Dow Chemical Co., Midland, Mich.), THIXATROL® (Elementis Company, Hightstown N.J.), and DIFFUSOL® (Transene Co. Inc., Danvers, Mass.).

Among commonly used organic thixotropic agents is hydrogenated castor oil and derivatives thereof. A thixotrope is not always necessary because the solvent coupled with the shear thinning inherent in any suspension can alone be suitable in this regard. Furthermore, wetting agents can be employed such as fatty acid esters, e.g., N-tallow-1,3-diaminopropane di-oleate; N-tallow trimethylene diamine diacetate; N-coco trimethylene diamine, beta diamines; N-oleyl trimethylene diamine; N-tallow trimethylene diamine; N-tallow trimethylene diamine dioleate, and combinations thereof.

Other Additives

Other inorganic additives can be added to the paste to the extent of about 0.5 to about 30 wt %, preferably about 2 to about 25 wt % and more preferably about 5 to about 20 wt % based on the weight of the paste prior to firing. Other additives such as clays, fine silicon, silica, or carbon, or combinations thereof can be added to control the reactivity of the aluminum with silicon. Common clays which have been calcined are suitable. Fine particles of low melting metal additives (i.e., elemental metallic additives as distinct from metal oxides) such as Pb, Bi, In, Zn, and Sb, and alloys of each can be added to provide a contact at a lower firing temperature, or to widen the firing window.

A mixture of (a) glasses or (b) crystalline additives and glasses or (c) one or more crystalline additives can be used to formulate a glass component in the desired compositional range. The goal is to improve the solar cell electrical performance. For example, second-phase crystalline ceramic materials such as $SiO_2$, ZnO, MgO, $ZrO_2$, $TiO_2$, $Al_2O_3$, $Bi_2O_3$, $V_2O_5$, $MoO_3$, $WO_3$, $CO_2O_3$, MnO, $Sb_2O_3$, SnO, $Tl_2O$, $TeO_2$, $GeO_2$ and $In_2O_3$ and reaction products thereof and combinations thereof can be added to the glass component to adjust contact properties. Ceramic additives include particles such as hectorite, talc, kaolin, attapulgite, bentonite, smectite, quartz, mica, feldspar, albite, orthoclase, anorthite, silica, and combinations thereof. Both crystalline and amorphous silica are suitable.

Paste Preparation

To prepare the paste compositions of the invention, the necessary frit or frits are ground to a fine powder using conventional techniques including milling. The frit component is then combined with the other components including aluminum. The solids are then mixed with the vehicle and the phosphorus compound to form the paste. In one embodiment, the paste can be prepared by a planetary mixer.

The viscosity of the paste can be adjusted as desired. In preparing the paste compositions, the particulate inorganic solids and the phosphorus compound are mixed with a vehicle and dispersed with suitable equipment, such as a planetary mixer, to form a suspension, resulting in a composition for which the viscosity will be in the range of about 200 to about 4000 poise, preferably about 500-1500 poise, more preferably 800-1200 poise at a shear rate of 9.6 $sec^{-1}$ as determined on a Brookfield viscometer HBT, spindle 14, measured at 25° C. Generally, when the back contact is only partially covered with the paste, the viscosity should be higher.

Printing and Firing of the Pastes

The inventive method of making a solar cell back contact involves providing a silicon substrate and a passivation layer thereon, applying the paste composition on the passivation layer, and heating the paste to sinter the conductive metal component and fuse the glass. In one embodiment, the method further involves making an Ag or Ag/Al back contact by applying an Ag or Ag/Al back contact paste on the back surface of the silicon substrate and heating the Ag or Ag/Al back contact paste. In another embodiment, the method further involves making an Ag front contact by applying an Ag front contact paste on the front surface of the silicon substrate and heating the Ag front contact paste.

The pastes can be applied by any suitable techniques including screen printing, inkjet printing, decal application, spraying, brushing, roller coating or the like. In one embodiment, screen printing is preferred. After application of the paste to a substrate in a desired pattern, the applied coating is then dried and fired to adhere the paste to the substrate. The firing temperature is generally determined by the frit maturing temperature, and preferably is in a broad temperature range. In one embodiment, solar cells with screen printed aluminum back contacts are fired to relatively low temperatures (550° C. to 850° C. wafer temperature; furnace set temperatures of 650° C. to 1000° C.) to form a low resistance contact between the P-side of a boron doped silicon wafer and an aluminum based paste. In another embodiment, the solar cell printed with the subject Al back contact paste, the Ag back contact paste, and the Ag front contact paste can be simultaneously fired at a suitable temperature, such as about 650-1000° C. furnace set temperature; or about 550-850° C. wafer temperature. During firing, the ARC is attacked and corroded by the paste; i.e., "fire-through." Also during firing as the wafer temperature rises above the Al—Si eutectic temperature of 577° C., the back contact Al dissolve Si from the substrate and to form a liquid layer including Al and Si.

This Al—Si liquid continues to dissolve substrate Si during further heating to peak temperature. During the cool down period, Si precipitates back from the Al—Si melt. This precipitating Si grows as an epitaxial layer on the underlying Si substrate and forms a p+ layer. When the cooling melt reaches the lowest eutectic temperature of Al—Si-metal melt, the remaining liquid freezes as an Al—Si-metal eutectic layer. A p+ layer is believed to provide a BSF, which in turn increases the solar cell performance. The glass in the Al back contact optimally interacts with both Al and Si without unduly affecting the formation of an efficient BSF layer.

The preferred embodiment for these pastes is fire-through the passivation layer such as SiNx. However these pastes can also be fired on the conventional laser fired (to open up holes in passivation layer) back passivated silicon solar cells too.

Method of Front and Back Contact Production

Referring now to FIGS. 1-5, one of many exemplary methods of making a solar cell Al back contact according to the present invention is illustrated. In this example, the method involves making an Ag or Ag/Al back contact and an Ag front contact also.

Figure 1:
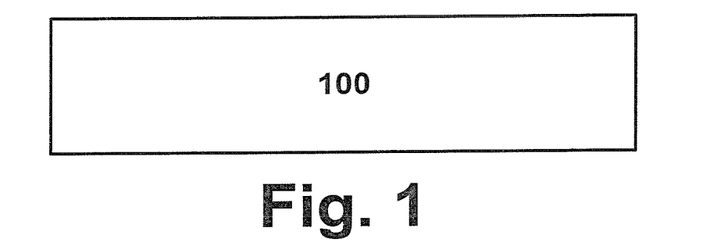

FIG. 1 schematically shows providing a substrate 100 of single-crystal silicon or multicrystalline silicon. The substrate typically has a textured surface which reduces light reflection. In the case of solar cells, substrates are often used as sliced from ingots which have been formed from pulling or casting processes. Substrate surface damage caused by tools such as a wire saw used for slicing and contamination from the wafer slicing step are typically removed by etching away about 10 to 20 microns of the substrate surface using an aqueous alkali solution such as KOH or NaOH, or using a mixture of HF and $HNO_3$. The substrate optionally can be washed with a mixture of HCl and $H_2O_2$ to remove heavy metals such as iron that can adhere to the substrate surface. An antireflective textured surface is sometimes formed thereafter using, for example, an aqueous alkali solution such as aqueous potassium hydroxide or aqueous sodium hydroxide. This gives the substrate, 100, depicted with exaggerated thickness dimensions. The substrate is typically a p-type silicon layer having about 200 microns or less of thickness.

Figure 2:
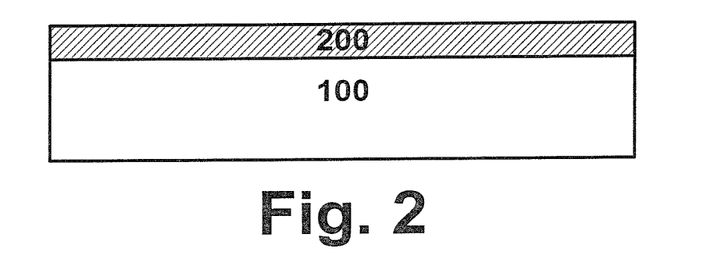

FIG. 2 schematically illustrates that, when a p-type substrate is used, an n-type layer 200 is formed to create a p-n junction. Examples of n-type layers include a phosphorus diffusion layer. The phosphorus diffusion layer can be supplied in any of a variety of suitable forms, including phosphorus oxychloride ($POCl_3$), and organophosphorus compounds. The phosphorus source can be selectively applied to only one side of the silicon wafer, e.g., a front side of the wafer. The depth of the diffusion layer can be varied by controlling the diffusion temperature and time, is generally about 0.2 to 0.5 microns, and has a sheet resistivity of about 40 to about 100 ohms per square. The phosphorus source can include phosphorus-containing liquid coating material. In one embodiment, phosphosilicate glass (PSG) is applied onto only one surface of the substrate by a process such as spin coating, where diffusion is effected by annealing under suitable conditions.

Figure 3:
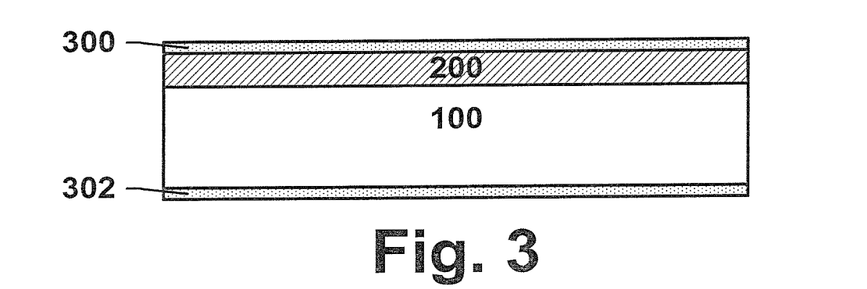

FIG. 3 schematically illustrates forming an antireflective coating (ARC) 300, which also usually serves as a passivation layer also on the above-described n-type diffusion layer 200. The ARC layer typically includes $SiN_x$, $TiO_2$, or $SiO_2$. A back passivation layer 302 is similarly applied to the back side of the silicon wafer 100. Silicon nitride is sometimes expressed as $SiN_x$:H to emphasize passivation by hydrogen. The ARC 300 reduces the surface reflectance of the solar cell to incident light, thus increasing the amount of light absorption, and thereby increasing the electrical current generated. The thickness of passivation layers 300 and 302 depends on the refractive index of the material applied, although a thickness of about 700 to 900 A is suitable for a refractive index of about 1.9 to 2.0.

The passivation layers 300 and 302 can be formed by a variety of procedures including low-pressure CVD, plasma CVD, or thermal CVD. When thermal CVD is used to form a $SiN_x$ coating, the starting materials are often dichlorosilane ($SiCl_2H_2$) and ammonia ($NH_3$) gas, and film formation is carried out at a temperature of at least 700° C. When thermal CVD is used, pyrolysis of the starting gases at the high temperature results in the presence of substantially no hydrogen in the silicon nitride film, giving a substantially stoichiometric compositional ratio between the silicon and the nitrogen, i.e., $Si_3N_4$.

Figure 4:
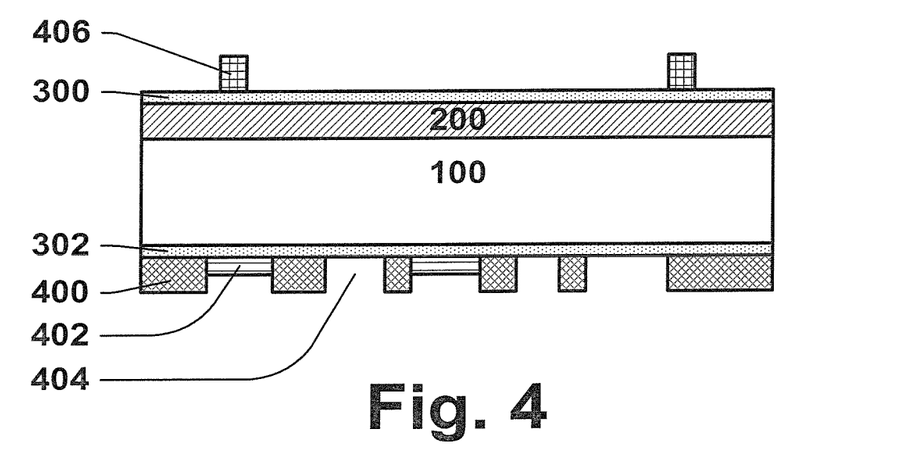

FIG. 4 schematically illustrates applying an Al back paste 400 and an Ag or Ag/Al back paste 402 on the back side of the substrate. The preferred Al back paste includes at least one phosphorous compound described herein and one or more glass frits from one or more of Tables 1-7. Al back paste without phosphorus compound but containing phosphate glass can also be used. The pastes can be applied selectively by screen printing and successively dried on the back side of the substrate. The back surface can be largely covered with the Al back paste, to a wet thickness of about 30 to 50 microns, owing in part to the need to form a thicker p+ layer subsequently. While not individually labeled, it is noted that FIG. 4 shows six segments of paste 400 applied to the backside of the silicon wafer 100. Gaps 404 between segments of pastes 400, 402 leave backside passivation layer 302 uncovered. An Ag front paste 406 for a front electrode is next screen printed and dried over the ARC 300. Firing is then carried out in an infrared belt furnace in a temperature range of approximately 700° C. to 1000° C. for a period of from about one to several minutes.

Figure 5:
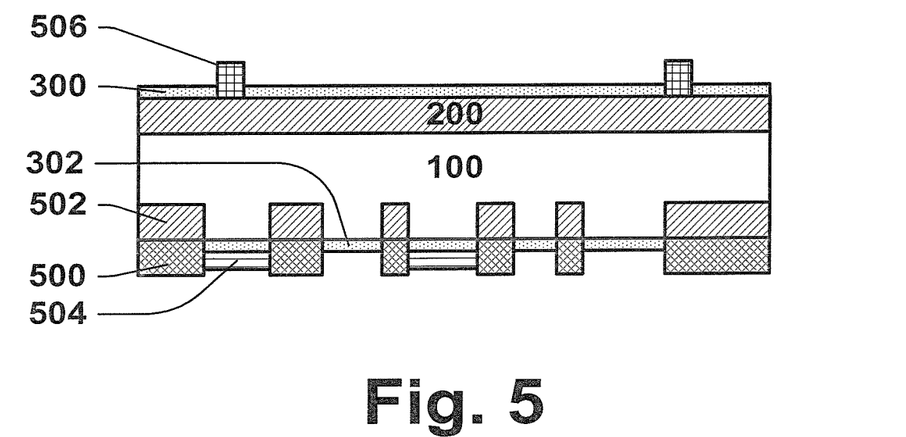

FIG. 5 schematically illustrates forming an Al back contact 500. The Al back paste is transformed by firing from a dried state 400 to an aluminum back contact 500. The Al back paste 400 sinters and penetrates through (i.e., fires through) the ARC layer 302 during firing, and is thereby able to electrically contact the p-type layer of the substrate 100. Since aluminum of the Al back paste can fire through the passivation layer 302, the method does not involve making a hole in the passivation layer 302 to apply a paste composition.

FIG. 5 further schematically illustrates forming a BSF layer 502. Aluminum of the Al paste 400 melts and reacts with the silicon substrate 100 during firing, then solidifies forming a partial p+ layer, 502, containing a high concentration of aluminum dopant. This layer is generally called the back surface field (BSF) layer, and helps to improve the energy conversion efficiency of the solar cell. FIG. 5 shows six segments of BSF layer 502, corresponding with the six segments of aluminum paste 400 applied in FIG. 4. The back passivation layer 302 remains essentially unchanged after firing in those areas where it was not covered by aluminum back paste 400 in FIG. 4.

The Ag or Ag/Al back paste 402 can be fired at the same time, becoming a Ag or Ag/Al back contact 504. During firing, the boundary between the Al back contact and the Ag or Ag/Al back contact can assume an alloy state, and can be also connected electrically. The Ag or Ag/Al back contact can be used for tab attachment during module fabrication. In addition, the front electrode-forming silver paste 406 sinters and penetrates through (i.e., fires through) the silicon nitride film 300 during firing, and can be thereby able to electrically contact the n-type layer 200, as shown by front electrodes 506 in FIG. 5.

A solar cell back contact according to the present invention can be produced by applying any Al paste disclosed herein, produced by mixing aluminum powders, with the phosphorous compounds and the glass compositions of Table 1, to the P-side of the silicon substrate, for example by screen printing, to a desired wet thickness, e.g., from about 30 to 50 microns. To make a front contact, front contact Ag pastes can be printed on the front side.

Automatic screen-printing techniques can be employed using a 200-325 mesh screen to apply the Al back paste on the back surface of the substrate. The printed pattern is then dried at about 200° C. or less, preferably at about 120° C. for about 5-15 minutes before firing. The dry printed Al back contact paste of the present invention can be co-fired with the silver rear contact and the front contact silver pastes for as little as 1 second up to about 5 minutes at peak temperature, in a belt conveyor furnace in air.

Nitrogen ($N_2$) or another inert atmosphere can be used if desired when firing. The firing is generally according to a temperature profile that will allow burnout of the organic matter at about 300° C. to about 550° C., a period of peak furnace set temperature of about 650° C. to about 1000° C., lasting as little as about 1 second, although longer firing times as high as 1, 3, or 5 minutes are possible when firing at lower temperatures. For example a three-zone firing profile can be used, with a belt speed of about 1 to about 4 meters (40-160 inches) per minute. Naturally, firing arrangements having more than 3 zones are envisioned by the present invention, including 4, 5, 6, or 7, zones or more, each with zone lengths of about 5 to about 20 inches and firing temperatures of 650 to 1000° C. In one embodiment, the Al back paste is fired using a typical firing profile of 550° C.-550° C.-550° C.-700° C.-800° C.-940° C. set in a 6-zone furnace with the belt speed of 180 inches per minute.

EXAMPLES

The following examples illustrate the subject invention. Unless otherwise indicated in the following examples and elsewhere in the specification and claims, all parts and percentages are by weight, all temperatures are in degrees Celsius, and pressure is at or near atmospheric pressure.

Exemplary paste compositions formulated and tested are shown in Tables 2 and 3. Al 5540 paste in Tables 2 and 3 includes 72% wt. % of Al and 28% wt. % of vehicle, which is commercially available from Ferro Corporation, Vista, Calif. Phosphate ester in Tables 2 and 3 is 2-ethylhexanol phosphate, with commercial name of 1861-2-EH321 (Custom Synthesis, LLC). The paste is applied on a SiNx back layer (i.e., back passivation layer) having a thickness of about 5-50 microns on a silicon wafer to form a paste layer having a thickness of 5-50 microns. Polycrystalline silicon wafers, used in the following examples were 243 $cm^2$ in area, about 180 microns thick, and had a sheet resistivity of 60 ohms per square. The Al back paste is printed on the back passivated side of the wafer, dried and fired. The pastes of Table 2 are fired in a six-zone infrared belt furnace with a belt speed of about 3.05 meters per minute, with temperature settings of 400° C., 400° C., 600° C., for first three zones, and 980° C. in last three zones, respectively. The pastes of Table 3 are fired in a six-zone infrared belt furnace with a belt speed of about 4.57 meters per minute, with temperature settings of the first three zones at 550° C., and last three zones of 700° C., 800° C., and 940° C., respectively. The lengths of the zones of the six-zone infrared belt furnace are 45.7, 45.7, 22.9, 22.9, 22.9, and 22.9 cm long, respectively. The details of paste preparation, printing, drying and firing can be found in commonly owned U.S. Patent Application Publication Nos. US2006/0102228 and US 2006/0289055, the disclosures of which are incorporated by reference.

The fired pastes are evaluated at two different peak set temperatures 980° C. and 940° C. to determine 1) whether the paste fires through the back passivation layer, 2) Al—Si eutectic formation is developed, 3) a BSF layer is formed at the back side of the substrate, and 4) a wider firing window is achieved. The results of the evaluation are shown in Tables 2 and 3.

TABLE 2

Fire-through Performance of Al back pastes fired at the peak set temperature of 980° C.

| Al back paste | Reference | 1 | 2 | 3 |
|---|---|---|---|---|
| Al 5540 (wt. %) | 100 | 90 | 90 | 80 |
| Phosphate ester (wt. %) | 0 | 10 | 0 | 10 |
| EG9111VWG (wt. %) | 0 | 0 | 10 | 10 |
| SiNx fire-through | No | Yes | Yes | Yes |
| Eutectic formulation | No | Yes | Yes | Yes |
| BSF formulation | No | Yes. Wide, long | Yes. Wide, long | Yes. Very wide, long |

TABLE 3

Fire-through Performance of Al back pastes fired at the peak set temperature of 940° C.

| Al back paste | Reference | 1 | 2 | 3 |
|---|---|---|---|---|
| Al 5540 (wt. %) | 100 | 90 | 90 | 80 |
| Phosphate ester (wt. %) | 0 | 10 | 0 | 10 |
| EG9111VWG (wt. %) | 0 | 0 | 10 | 10 |
| SiNx fire-through | No | Yes | Yes | Yes |
| Eutectic formulation | No | Yes | Yes | Yes |
| BSF formulation | No | Yes. Thin, short | Yes. Thin, short | Yes. Thin, short |

The results in Tables 2 & 3 show that fire-through, sufficient eutectic and good BSF formation are achieved by the inventive pastes 1 to 3 compared to the reference paste. Further the inventive pastes seem to have a reasonable firing window.

What has been described above includes examples of the subject invention. It is, of course, not possible to describe every conceivable combination of components or methodologies for purposes of describing the subject invention, but one of ordinary skill in the art may recognize that many further combinations and permutations of the subject invention are possible. Accordingly, the subject invention is intended to embrace all such alterations, modifications and variations that fall within the spirit and scope of the appended claims. Furthermore, the foregoing ranges (e.g., compositional ranges and conditional ranges) are preferred and it is not the intention to be limited to these ranges where one of ordinary skill in the art would recognize that these ranges may vary depending upon specific applications, specific components and conditions for processing and forming the end products. Disclosure of a range constitutes disclosure of each discrete value within such range, and subranges within the range. One range can be combined with another range. Disclosure of a Markush group supports each individual member of such group and any subgrouping within such group. To the extent that the terms "contain," "have," "include," and "involve" are used in either the detailed description or the claims, such terms are intended to be inclusive in a manner similar to the term "comprising" as "comprising" is interpreted when employed as a transitional word in a claim. In some instances, however, to the extent that the terms "contain," "have," "include," and "involve" are used in either the detailed description or the claims, such terms are intended to be partially or entirely exclusive in a manner similar to the terms "consisting of" or "consisting essentially of" as "consisting of" or "consisting essentially of" are interpreted when employed as a transitional word in a claim.

What is claimed is:

1. A paste composition comprising:
    about 40 to about 80 wt % of a conductive metal component consisting of aluminum;
    a glass component comprising a phosphate glass comprising 20-25 mol % PbO, 55-65 mol % $V_2O_5$, and 15-20 mol % $P_2O_5$;
    about 10 to about 30 wt % of an organic phosphorus compound comprising an organic phosphate; and
    a vehicle.

2. The paste composition of claim 1, further comprising: at least one phosphorus compound selected from the group consisting of ammonium phosphates, ammonium phosphonates, organic phosphonates, ammonium salts of organic phosphonates, alkali metal salts of organic phosphonates, alkaline earth metal salts of organic phosphonates, ammonium hypophosphites, organic hypophosphites, ammonium salts of organic hypophosphites, alkali metal salts of organic hypophosphites, and alkaline earth metal salts of organic hypophosphites.

3. The paste composition of claim 2, wherein the paste composition further comprises an ammonium hypophosphite, and the ammonium hypophosphite is selected from the group consisting of ammonium dihydrogen phosphate and diammonium hydrogen phosphate.

4. The paste composition of claim 2, wherein the paste composition further comprises an organic phosphate, organic phosphonate, or organic hypophosphite, and the organic phosphate, organic phosphonate, or organic hypophosphite has the formula $Y_n(XO)_{3-n}P=O$, wherein n=0, 1, or 2, and X and Y are each independently selected from the any group consisting of a hydrogen, alkyl, cycloalkyl, aryl, alkaryl, aralkyl, and aromatic group.

5. The paste composition of claim 2, wherein the paste composition further comprises an organic phosphonate, and the organic phosphonate is at least one selected from the group consisting of $C_1$ to $C_{20}$ alkyl phosphonates, $C_3$ to $C_8$ cycloalkyl phosphonates, $C_6$ to $C_{12}$ aryl phosphonates, and $C_7$ to $C_{20}$ aralkyl phosphonates.

6. The paste composition of claim 2, wherein the paste composition further comprises an organic hypophosphite, and the organic hypophosphite is at least one selected from the group consisting of $C_1$ to $C_{20}$ alkyl hypophosphites, $C_3$ to $C_8$ cycloalkyl hypophosphites, $C_6$ to $C_{12}$ aryl hypophosphites, and $C_7$ to $C_{20}$ aralkyl hypophosphites.

7. The paste composition of claim 1, wherein the organic phosphate is at least one selected from the group consisting of $C_1$ to $C_{20}$ alkyl phosphates, $C_3$ to $C_8$ cycloalkyl phosphates, $C_6$ to $C_{12}$ aryl phosphates, and $C_7$ to $C_{20}$ aralkyl phosphates.

8. The paste composition of claim 1, wherein the paste composition comprises:
    about 0.5 to about 10 wt % of the glass component; and
    about 15 to about 40 wt % of the vehicle.

9. The paste composition of claim 1, wherein the glass component further comprises a glass frit comprising from about 25 mole % to about 65 mole % of $Bi_2O_3$, from about 3 mole % to about 60 mole % of ZnO, and from about 4 mole % to about 65 mole % of $B_2O_3$.

10. The paste composition of claim 1, wherein the glass component further comprises a glass frit comprising from about 25 mole % to about 65 mole % of $Bi_2O_3$, from about 4 mole % to about 65 mole % of $B_2O_3$, and from about 5 mole % to about 35 mole % of $SiO_2$.

11. The paste composition of claim 1, wherein the glass component further comprises a glass frit comprising from about 3 mole % to about 60 mole % of ZnO, from about 4 mole % to about 65 mole % of $B_2O_3$, and from about 5 mole % to about 35 mole % of $SiO_2$.

12. The paste composition of claim 1, wherein the glass component further comprises a glass frit comprising from about 5 mole % to about 55 mole % of $Li_2O+Na_2O+K_2O$, from about 0.5 mole % to about 25 mole % of $TiO_2$, from about 5 mole % to about 75 mole % of $B_2O_3+SiO_2$, from about 0 mole % to about 20 mole % of $MgO+CaO+BaO+SrO$, and from about 0 mole % to about 20 mol % F.

13. The paste composition of claim 1, wherein the glass component further comprises a glass frit comprising from about 5 mole % to about 85 mole % of $Bi_2O_3$, from about 5 mole % to about 35 mole % of $SiO_2$, and from about 0 mole % to about 55 mole % of ZnO.

14. The paste composition of claim 1, wherein the glass component further comprises a glass frit comprising from about 5 mole % to about 35 mole % of $B_2O_3+SiO_2$, and from about 1 mole % to about 25 mole of $Al_2O_3$.

15. A photovoltaic cell comprising a silicon wafer and a back contact thereon, the back contact comprising a passivation layer at least partially coated with a fired back side paste, the back side paste comprising, prior to firing:
    about 40 to about 80 wt % of a conductive metal component consisting of aluminum;
    a glass component comprising a phosphate glass comprising 20-25 mol % PbO, 55-65 mol % $V_2O_5$, and 15-20 mol % $P_2O_5$;
    about 10 to about 30 wt % of an organic phosphorus compound comprising an organic phosphate; and
    a vehicle.

16. A method of making a paste composition, comprising:
    combining about 40 to about 80 wt % of a conductive metal component consisting of aluminum, a glass component comprising a phosphate glass comprising 20-25 mol % PbO, 55-65 mol % $V_2O_5$, and 15-20 mol %

$P_2O_5$, about 10 to about 30 wt % of an organic phosphorus compound comprising an organic phosphate, and a vehicle; and dispersing the conductive metal component, the organic phosphorus compound, and the glass component in the vehicle.

17. The method of claim 16, wherein the at least one phosphorus compound further comprises ammonium phosphates, ammonium phosphonates, organic phosphonates, ammonium salts of organic phosphonates, alkali metal salts of organic phosphonates, alkaline earth metal salts of organic phosphonates, ammonium hypophosphites, organic hypophosphites, ammonium salts of organic hypophosphites, alkali metal salts of organic hypophosphites, and alkaline earth meal salts of organic hypophosphites.

\* \* \* \* \*